(12) United States Patent
Neuberger

(10) Patent No.: US 6,343,174 B1
(45) Date of Patent: Jan. 29, 2002

(54) LASER DELIVERY SYSTEM WITH OPTICAL FIBERS HAVING FLUID DELIVERY CHANNELS

(75) Inventor: Wolfgang Neuberger, F.T. Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/364,960

(22) Filed: Jul. 30, 1999

(51) Int. Cl.[7] .............................. G02B 6/02; G02B 6/06; A61B 18/18; A61B 17/36
(52) U.S. Cl. ........................ 385/123; 385/125; 385/126; 385/117; 606/15; 606/16; 606/21; 604/20; 604/21
(58) Field of Search ................................. 385/117, 123, 385/118, 115, 124, 125–127; 606/15, 16, 7, 13, 20, 21, 30, 31, 49, 53, 22, 65–67; 604/20–21

(56) References Cited

U.S. PATENT DOCUMENTS

| | | | |
|---|---|---|---|
| 4,707,073 A | | 11/1987 | Kocher |
| 4,764,194 A | | 8/1988 | Maklad |
| 5,203,780 A | | 4/1993 | Liebler |
| 5,246,437 A | * | 9/1993 | Abela ............................. 606/5 |
| 5,471,553 A | | 11/1995 | Teshima |
| 5,571,151 A | * | 11/1996 | Gregory ....................... 606/15 |
| 5,840,059 A | * | 11/1998 | March et al. .................. 606/45 |
| 5,999,678 A | * | 12/1999 | Murphy-Chutorian et al. ... 385/117 |

* cited by examiner

*Primary Examiner*—Hemang Sanghavi
(74) *Attorney, Agent, or Firm*—Bolesh J. Skutnik; B J Associates

(57) ABSTRACT

Briefly stated, the present invention provides a medical laser delivery system that incorporates fluid delivery channels within the optical fiber structure so as to bring fluids directly to the site of laser power delivery. The channel or channels may pass through either the fiber core or the cladding. The fluids delivered to the site may serve to cool or irrigate the tissue during high power laser treatment. In addition, the fluid passed through the channel can be a drug or any substance that increases the tissue's photosensitivity to the laser energy. The need for an external fluid delivery device is eliminated. Treatment with the system is minimally invasive. Treatment and irrigation of the treatment site can be administered through a single fiber thereby limiting the entry puncture to the gauge of the fiber. The solid core fiber coupled with direct irrigation allows effective high-power density laser treatment. High-powered laser treatment is efficient and therefore provides for a shorter surgery time. The invention allows for a maximal delivery of fluids for irrigation, cooling, and/or photosensitizing to a site, with a minimal amount of invasiveness and an efficient high-power laser treatment.

18 Claims, 4 Drawing Sheets

LASER DELIVERY SYSTEM WITH OPTICAL FIBERS HAVING FLUID DELIVERY CHANNELS

BACKGROUND OF THE INVENTION

1. Field of the Invention

The invention relates generally to medical optical fiber laser systems requiring fluid delivery, and more specifically to laser delivery fibers that incorporate fluid delivery channels within the fiber.

2. Invention Disclosure Statement

Laser systems can operate as beneficial and effective medical instruments. They allow specific treatment to be administered with minimal invasiveness. Medical laser systems frequently require cooling or irrigation at the distal (output) end of the optical fiber, as well as the site of laser power delivery. Presently, this requires additional channels outside the optical fiber to deliver the fluid. However, irrigation doesn't reach the treatment site as effectively as desired if it is delivered proximally but not directly to the area of laser power treatment. Similarly, hollow optical fibers may be used. With these fibers, the laser power is delivered through a central hollow core. If hollow optical fibers are used, a gaseous medium can also be passed through the fiber's hollow center along with the laser energy. However, hollow optical fibers are typically limited to $CO_2$ laser delivery and therefore to certain wavelength and physical effects caused by this radiation. For instance, the gaseous medium employed cannot absorb light at the same wavelength as the laser because it might then interfere with delivery of the laser energy.

Medical laser delivery systems employing external irrigating or cooling channels often require the insertion of a catheter into the body through which interchangeable components are inserted. This system generally necessitates a large entry hole to accommodate a large bore catheter to serve as a channel for all the components. Use of this system inevitably increases the surgery time, simply by the fact that the operator must remove and insert varying components into the catheter sheath. A sampling of such inventions is provided below.

U.S. Pat. No. 5,203,780 describes a device for venting laser smoke plumes generated by laser treatment of body tissues. The smoke is directed away from the treatment site through a venting space surrounding the optical fiber; driven by an external vacuum. The device however, involves placing a catheter containing an insertion needle into the treatment site, removing the needle component, and then placing in the desired optical lasing device. By necessity, the bore of the catheter must be larger than that of the treatment fiber resulting in the need for a larger entry hole. In addition, for this particular invention, the space between the wall of the catheter and the optical fiber serves as a conduit for the vacuum to draw smoke from the site. The presence of that space requires that the bore of the catheter be even larger. A typical example of this type of device can be seen in FIG. 1. There, optical fiber 2 is passed through catheter 1 while catheter distal end 3 is inserted into tissue 4. The entry hole has to be larger than the bore of fiber 2 to accommodate distal end of the catheter 3. Should device 100 function also to deliver or remove fluid from the treatment site, then catheter bore and insertion hole will be even greater in order to allow a passageway around fiber 2 and into catheter 1. Two additional factors of a typical device would increase the bore size of catheter 1. First, to prevent the collapse of catheter 1 if a vacuum were applied to device 100 would require thicker walls and hence a greater bore. Second, to prevent movement of optical fiber 2 inside catheter 1 and to maintain a uniform passage space around optical fiber 2, there must be ribbing 5 within catheter 1 to prevent kinking or twisting of optical fiber 2.

U.S. Pat. No. 4,707,073 describes a non-medical system for the delivery of a high power laser through an optical fiber for use in cutting, drilling, or welding metal where the fiber (and subsequently the work material) is cooled by gas passed coaxially over it. This is achieved through an outer tube surrounding the fiber into which gas is injected. The gas travels along the outer length of the fiber and is emitted out onto the work surface. The system however, provides only a broad exposure of the coolant to the surface receiving the laser energy. The cooling effect is therefore unfocused and non-specific. Applications requiring a more directed coolant would need a specific, and controlled delivery. Further, by having an external coolant-delivery component, it increases the overall diameter of the delivery fiber which in turn decreases the fiber's flexibility and makes use of the device more cumbersome.

U.S. Pat. No. 4,764,194 describes a process for the production of optical fibers wherein a hollow channel comprises the core, surrounded by a layer of cladding material. Hollow optical fibers have been employed in situations where they are needed to carry a wavelength that is difficult to transmit through a solid core optical fiber. For example, utilizing a hollow optical fiber when transmitting a mid-infrared laser. However, wavelengths in the ultraviolet, visible and near-visible IR regions are better transmitted through a solid core fiber, such as a silica fiber. Therefore, the advantages of using a hollow core fiber are highly restricted to certain wavelength transmissions. For most applications, a hollow optical fiber would perform poorly in comparison to a solid counterpart. It would be advantageous to have a system that employs a solid fiber to deliver the energy. The present proposed invention includes a solid laser delivery optical fiber.

U.S. Pat. No. 5,471,553 describes a method for the preparation of light-guide fibers containing a central hollow area surrounded by a peripheral resin layer containing a multiple arrangement of cores. The multicore hollow optical fiber can be used as a compact light guide for devices inserted in its hollow channel (i.e. an endoscope, a laser, an optical fiber, etc.). The hollow channel does not deliver any cooling media nor do the multicore fibers function for anything more than a light-guide. The device then increases the treatment time by requiring the insertion of various implements through the channel.

Further, the hollow fiber described is constructed out of plastic, whereas the present invention calls for fabrication of the fibers out of silica glass. Plastic and glass are very different materials as are the fibers that they comprise. For example, production conditions such as the softening temperature are distinct. Therefore, the use of a plastic optical fiber for instance, precludes any application requiring a glass optical fiber instead.

The present invention describes a device and method to overcome the abovementioned limitations by providing a system that incorporates fluid delivery channels within a solid core optical fiber.

OBJECT AND SUMMARY OF THE INVENTION

It is an aim of the present invention to describe a method and device to deliver a fluid (gas, pure liquid, suspension, emulsion, or solution) through an optical fiber that has at least one core section guiding the laser radiation as well as fluid delivery channel or channels within the fiber to provide a conduit for the medium to be delivered to the treatment site at or close to its distal end.

It is another aim of the present invention to place fluid delivery channel or channels within the cladding layer of the optical fiber.

It is a further aim of the present invention to place fluid delivery channel or channels within the core of the optical fiber in which case, the laser energy may be coupled to the delivery system through a suitable ring mode coupler.

It is also an aim of the present invention to place an independent cladding layer, separate from the cladding of the fiber, encompassing any delivery channels within the core to prevent evanescent waves from interfering with delivery of the laser power.

Still another aim of the present invention is to pass fluids through the delivery channels to irrigate or cool the site of laser delivery; in addition the fluid can be a photosensitizer that would enhance the treated tissue's sensitivity to the laser power leading to singlet oxygen formation during photodynamic therapy used to destroy tumors and kill bacteria.

Briefly stated, the present invention provides a medical laser delivery system that incorporates fluid delivery channels within an optical fiber structure so as to bring fluids directly to the site of laser power delivery. The channel or channels may pass through either the fiber core or the cladding. The fluids delivered to the site may serve to cool or irrigate the tissue during high power laser treatment. In addition, the fluid passed through the channel can be a drug or any substance that increases the tissue's photosensitivity to the laser energy. The need for an external fluid delivery device is eliminated. Treatment with the system is minimally invasive. Treatment and irrigation of the treatment site can be administered through a single fiber thereby limiting the entry puncture to the gauge of the fiber. The solid core fiber coupled with direct irrigation allows effective high-power density laser treatment. High-powered laser treatment is efficient and therefore provides for a shorter surgery time. The invention allows for a maximal delivery of fluids for irrigation, cooling, and/or photosensitizing to a site, with a minimal amount of invasiveness and an efficient high-power laser treatment.

The above, and other objects, features and advantages of the present invention will become apparent from the following description read in conjunction with the accompanying drawings, in which like reference numbers in different drawings denote like items.

DETAILED DESCRIPTION OF THE PREFERRED EMBODIMENTS

The present invention describes a new system for the incorporation of fluid delivery channels in medical laser treatment optical fibers. The proposed invention allows the delivery of irrigating, cooling or photosensitizing fluids to treatment sites in the vicinity of the fiber's distal end. By incorporating the delivery channels into the optical fiber itself, two advantages are achieved. First, the fluid can be introduced directly to the site of laser power delivery, where it is most needed. Second, treatment is minimally invasive; by placing the delivery channels within the fiber the insertion made in the treatment area need only be the diameter of the actual fiber. If the device were to have an external fluid delivery system, then the insertion opening would have to be larger to accommodate the extra delivery component.

The device employs an optical fiber with a solid core that incorporates fluid delivery channel or channels within either the core or the cladding. When the channels are included in the core, there may be an additional layer of cladding at the core/channel interface, encompassing each channel individually, separate from the fiber cladding; preventing evanescent waves from escaping into these channels. The channels are connected to a fluid source and a laser source at the proximal end of the fiber. If multiple channels within a single fiber exist there can be a common fluid source for the channels, or a separate fluid source for each individual channel. Individual fluid sources would allow the user to administer more than one fluid compound in one single treatment.

When the fluid delivery channels are present in the optical fiber's core, an optical coupler may be required to introduce the power from the laser source to the fiber's core.

Figure 1:
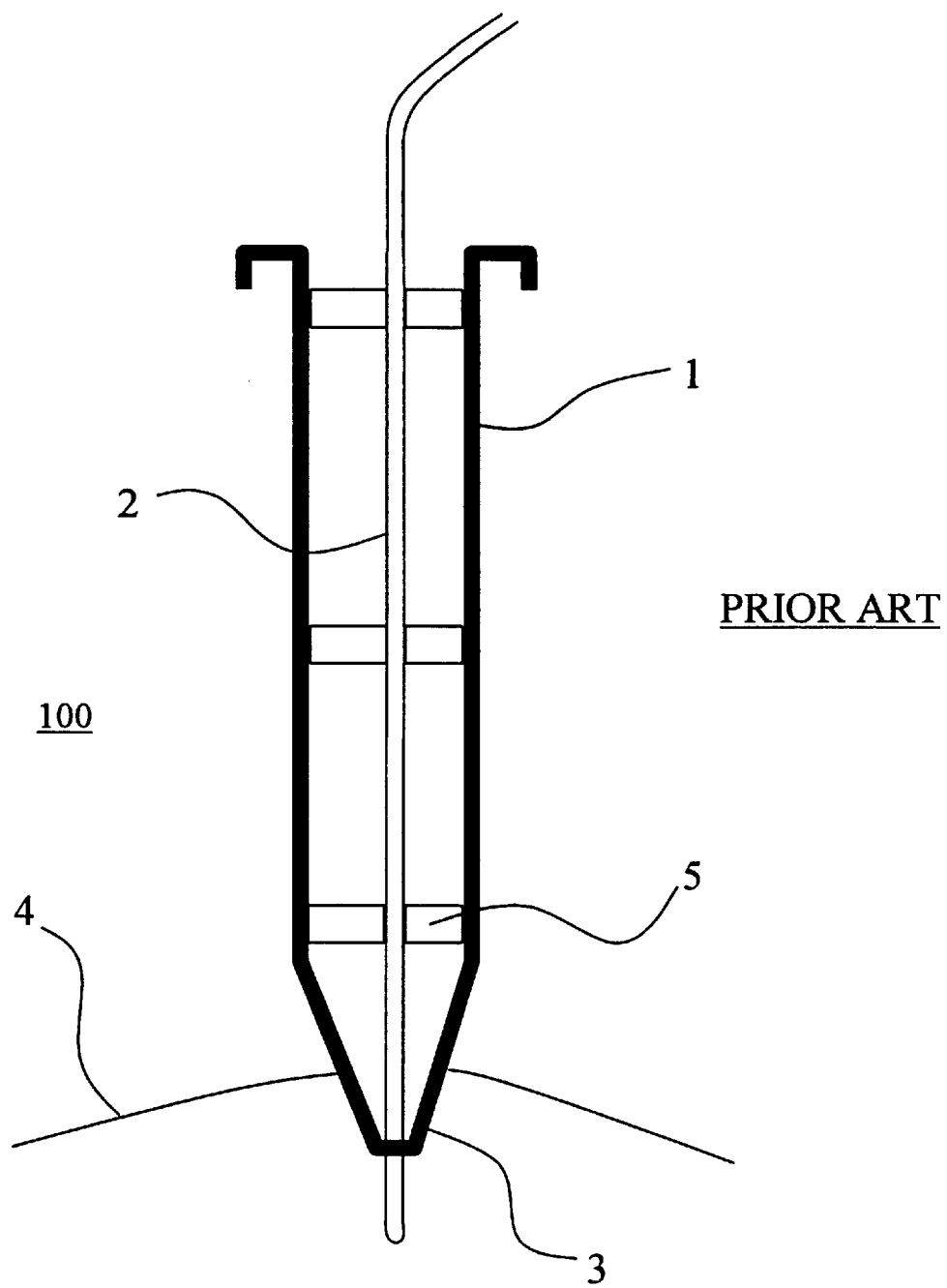
FIG. 1 shows a depiction of a prior art optical laser system with a fluid transport component.
Figure 2:
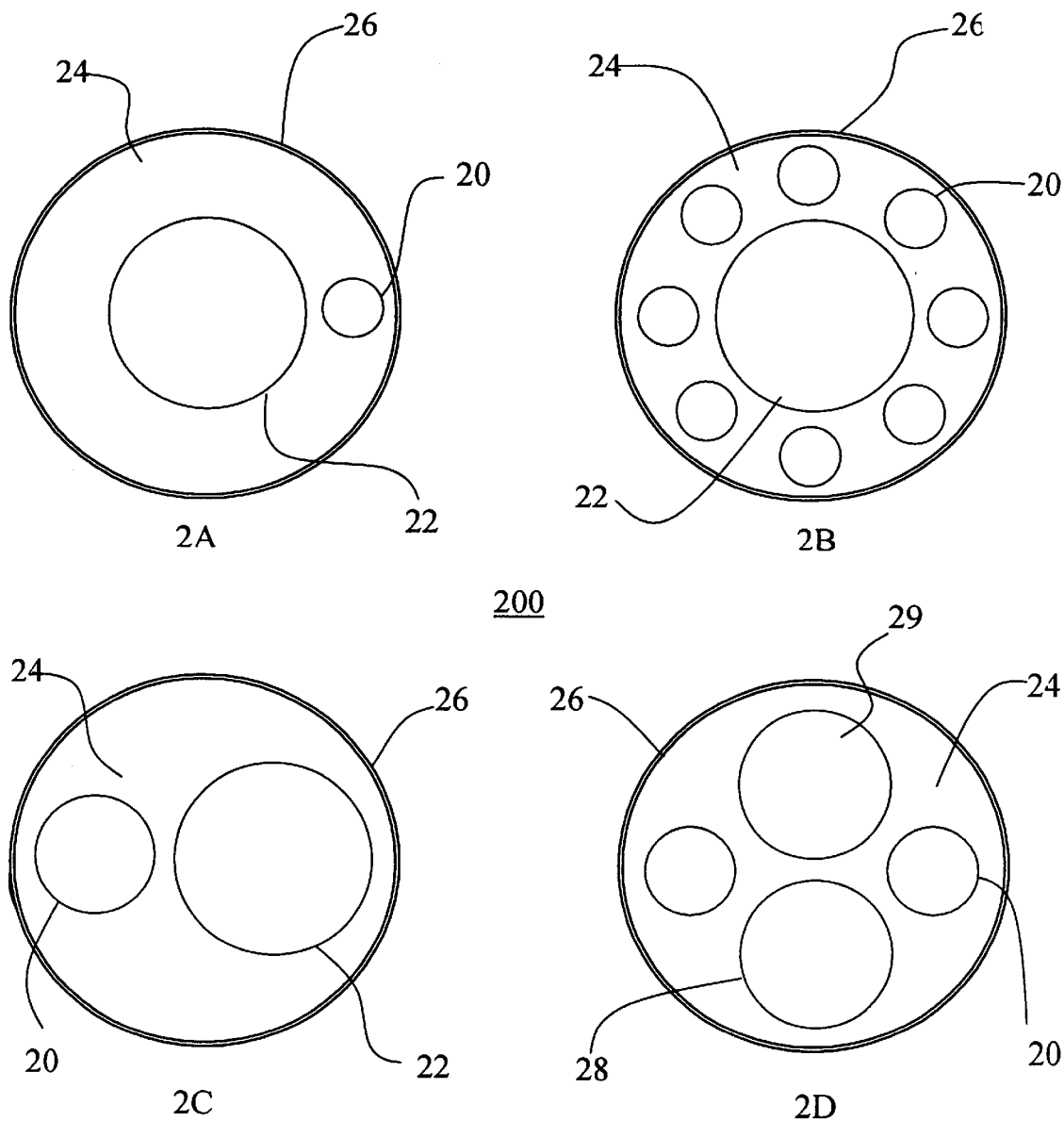
FIG. 2 is comprised of FIGS. 2A, 2B, 2C, and 2D. These show cross sectional views of an optical fiber with delivery channel or channels running longitudinally through the cladding.

FIG. 2 shows some preferred embodiments of the present invention displaying variations in the placement of the delivery channels within the cladding. The radius of the cladding is, as is typical with such delivery fibers, 20% greater than the radius of the core. In turn, the radius of the core is typically larger than the radius of the delivery channel or channels. When the delivery channels are present in the cladding layer of the optical fiber the radius of the channels must be significantly smaller than the thickness of the cladding layer surrounding it. This ensures that the channel will not protrude out of the cladding, or deform the shape of the cladding in any way. FIG. 2A shows a cross-sectional depiction of optical laser delivery fiber 200 comprised of outer jacket 26 surrounding cladding layer 24 and solid, central core 22. Within cladding 24, is delivery channel 20 that runs through fiber. Delivery channel 20 is a hole that runs longitudinally through fiber, parallel to core 22. FIG. 2B shows a cross-sectional depiction of an optical laser delivery fiber comprised of jacket 26 surrounding cladding layer 24 and solid, central core 22. Within cladding 24 are multiple hollow delivery channels 20. Each delivery channel 20 runs longitudinally through fiber, parallel to core 22. It is understood that placing multiple delivery channels 20 within cladding 24 can cause the refractive index of cladding 24 to change. It is not the intention of the present invention to change the refractive index of cladding layer 24 and therefore, the number of delivery channels 20 placed in cladding 24 should be limited as not to alter any of its properties. FIG. 2C shows a cross-sectional depiction of an optical laser delivery fiber comprised of jacket 26 surrounding cladding layer 24 and solid core 22. Included in cladding layer 24 is fluid delivery channel 20. Channel 20 runs through cladding layer 24 longitudinally, parallel to core 22. Core 22 is offset from the central axis of the fiber, adjacent to delivery channel 20. FIG. 2D shows a cross-sectional depiction of a multi-core optical laser delivery fiber comprised of jacket 26 surrounding cladding layer 24 and two solid cores 28 and 29 which may not be the same as core 22 depicted in the other embodiments in FIG. 2. Included in cladding layer 24 are two delivery channels 20. Each delivery channel 20 runs longitudinally through the fiber, parallel to cores 28 and 29.

Figure 3:
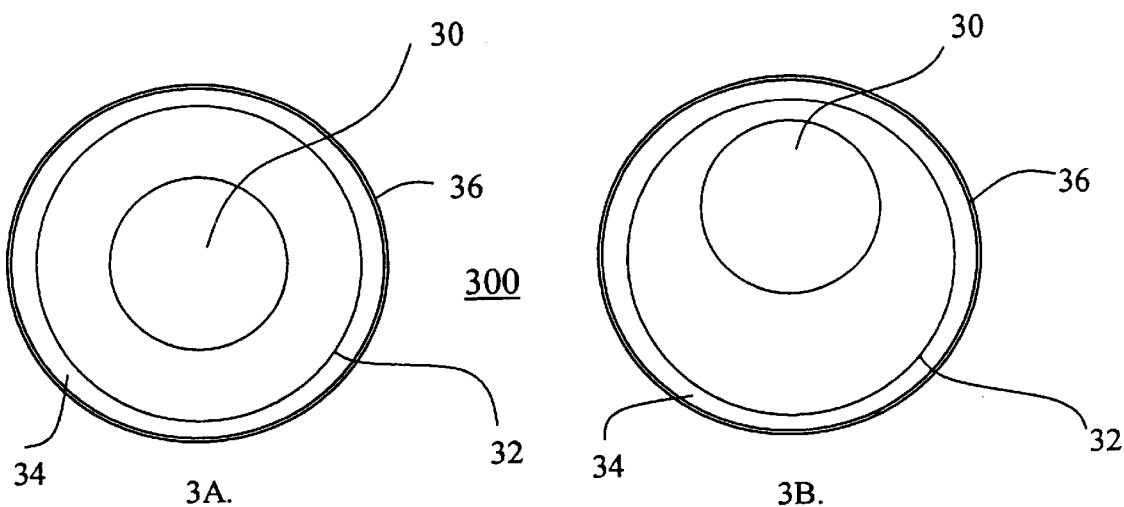
FIG. 3 is comprised of FIGS. 3A and 3B. These show cross sectional views of several preferred embodiments of an optical fiber with delivery channel or channels running longitudinally through the core.

FIG. 3 shows several preferred embodiments of optical delivery fiber 300 where a fluid delivery channel is located within the fiber core. FIG. 3A shows cross-sectional depiction of an optical laser delivery fiber comprised of jacket 36 surrounding cladding layer 34 and central core 32. Within core 32 is centrally situated fluid delivery channel 30. Delivery channel 30 runs longitudinally through the fiber, parallel to the axis of fiber 300. FIG. 3B shows a cross-sectional depiction of an optical laser delivery fiber comprised of jacket 36 surrounding cladding layer 34 and central core 32. Within core 32 is fluid delivery channel 30 offset from the center of core 32. Delivery channel 30 runs longitudinally through the fiber, parallel to the axis of fiber 300.

Figure 4:
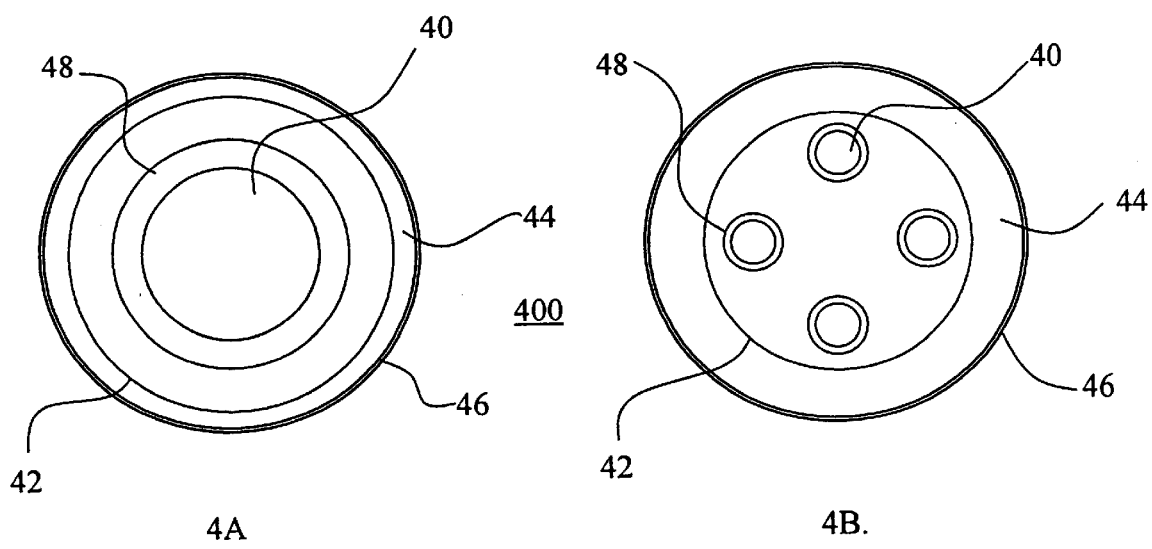
FIG. 4 is comprised of FIGS. 4A and 4B. These show cross sectional views of several preferred embodiments of an optical fiber with delivery channel or channels running longitudinally through the core, each of which are surrounded by a cladding layer.

FIG. 4 shows several more preferred embodiments of optical delivery fiber 400 where an additional cladding layer is added around the channels located in the core. FIG. 4A shows cross-sectional depiction of an optical laser delivery fiber comprised of jacket 46 surrounding cladding layer 44 and central core 42. Delivery channel 40 runs longitudinally through the fiber, parallel to the axis of fiber 400. Surrounding delivery channel 40 is inner cladding layer 48. Inner cladding layer 48 is distinct from fiber cladding layer 44 in that inner cladding layer 48 has lower index of refraction than that of core 42. Inner cladding layer 48 prevents evanescent waves from escaping into delivery channel 40 and thereby diminishing the wave in core 42. FIG. 4B shows cross-sectional depiction of an optical laser delivery fiber comprised of jacket 46 surrounding cladding layer 44 and central core 42. Contained within core 42 are multiple delivery channels 40 each surrounded by inner cladding layer 48. Delivery channels 40 run longitudinally through the fiber, parallel to the axis of fiber 400. Inner cladding layer 48 is distinct from fiber cladding layer 44.

Figure 5:
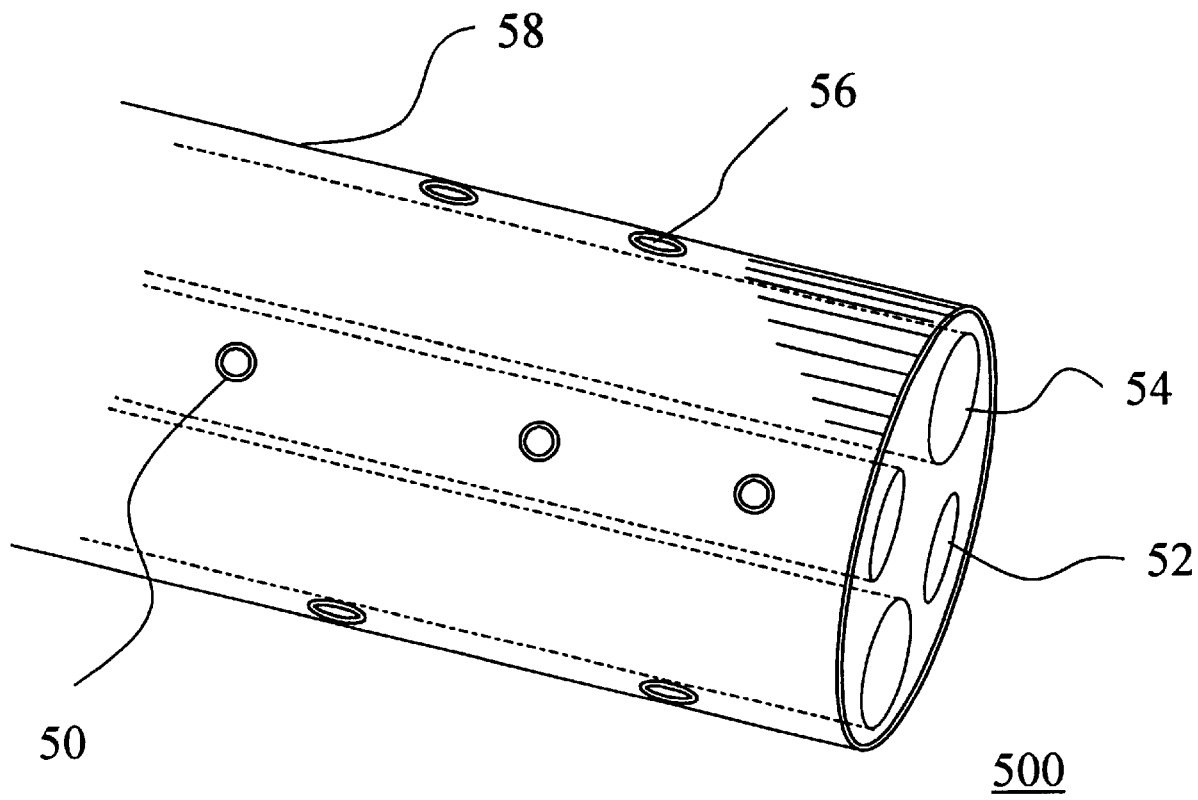
FIG. 5 shows a variation of an optical fiber with dispersion outlets on its distal end.

FIG. 5 shows a variation of the present invention wherein distal end 500 of optical fiber 58 has dispersion outlets 56 and 50 that disperse radiation and fluid, respectively, radially from distal end 500. Optical fiber 58 has within it radiation delivering cores 54 and fluid delivery channels 52. Approximately the last 2 cm of optical fiber 58 has dispersion outlets 50 and 56, i.e. randomly placed holes that run perpendicular to the axis of optical fiber 58 and into fiber cores 54 and fluid delivery channels 52. Dispersion outlet 56 provides an outlet for radiation traveling through core 54 to be dispersed radially from optical fiber 58. Similarly, dispersion outlet 50 provides an outlet for fluid travelling through delivery channel 52 to be dispersed radially from optical fiber 58. A related variation would involve "roughening" or "scoring" the core surface within dispersion outlet 56 to increase the radiation dispersal.

Having described preferred embodiments of the invention with reference to the accompanying drawings, it is to be understood that the invention is not limited to the precise embodiments, and that various changes and modifications may be effected therein by one skilled in the art without departing from the scope or spirit of the invention as defined in the appended claims.

What is claimed is:

1. A laser delivery optical fiber comprising:
   a central axis along its length, a core, a cladding, a distal end and a proximal end; said
   proximal end optically able to be coupled to a laser source;
   at least one longitudinal hole within said optical fiber capable of transferring a fluid medium from said optical fiber's proximal end to said optical fiber's distal end;
   said at least one longitudinal hole oriented parallel to said fiber's central axis; and said hole being smaller in radius than said core's radius or said cladding's thickness.

2. A laser delivery optical fiber according to claim 1, wherein said at least one longitudinal hole lies within said core of said optical fiber.

3. A laser delivery optical fiber according to claim 2, wherein said at least one longitudinal hole within said core of said optical fiber is lined with an inner cladding material, whose index of refraction is lower than that of said core.

4. A laser delivery optical fiber according to claim 1, wherein said at least one longitudinal hole lies within said cladding of said optical fiber.

5. A laser delivery fiber according to claim 1, wherein said at least one longitudinal hole is a plurality of longitudinal holes, all of which are within said cladding of said optical fiber.

6. A laser delivery optical fiber according to claim 1, wherein said core's axis does not coincide with said central axis of said optical fiber.

7. A laser delivery optical fiber according to claim 6, wherein said optical fiber further comprises a second core within said cladding both cores run longitudinally parallel to said central axis of said optical fiber.

8. A laser delivery system with at least one optical fiber having a core and a cladding, wherein said at least one optical fiber comprises:
   a distal end and a proximal end, and a central axis along its length;
   said proximal end being optically connected to a laser source;
   at least one longitudinal hole within said at least one optical fiber;
   said at least one longitudinal hole oriented parallel to said fiber's central axis;
   said hole being smaller in radius than said core's radius or said cladding's thickness; and
   said proximal end of said optical fiber being connected to a source of a fluid medium, which said at least one longitudinal hole transports to a site in close vicinity of said at least one optical fiber's distal end.

9. A laser delivery system according to claim 8, wherein said fluid medium is a gas.

10. A laser delivery system according to claim 8, wherein said fluid medium is a liquid.

11. A laser delivery system according to claim 8, wherein said fluid medium is selected from the group, a solution, an emulsion, and a suspension.

12. A laser delivery system according to claim 8, wherein said at least one longitudinal hole lies within said core of said optical fiber.

13. A laser delivery system according to claim 12, wherein said at least one longitudinal hole within said core of said optical fiber is lined with an inner cladding material, whose index of refraction is lower than that of said core.

14. A laser delivery optical fiber according to claim 8, wherein said at least one longitudinal hole lies within said cladding of said optical fiber.

15. A laser delivery system according to claim 8, wherein said at least one longitudinal hole is a plurality of longitudinal holes, all of which are within said cladding of said optical fiber.

16. A laser delivery system according to claim 8, wherein said core's axis does not coincide with said central axis of said optical fiber.

17. A laser delivery system according to claim 16, wherein said optical fiber further comprises a second core within said cladding both cores run longitudinally parallel to said central axis of said optical fiber.

18. A laser delivery system according to claim 8 further comprising: means for radial fluid dispersion as well as radial radiation dispersion in close proximity to said optical fiber's distal end.

* * * * *